United States Patent [19]

Wakatsuki et al.

[11] Patent Number: 5,082,635
[45] Date of Patent: Jan. 21, 1992

[54] HIGH-PRESSURE CRYSTALLOGRAPHIC OBSERVATION APPARATUS

[75] Inventors: Masao Wakatsuki; Kaoru Takano, both of Tsukuba; Kazuo Kitagawa, Kobe; Katsufumi Urabe, Ashiya; Toshimitsu Ishida, Akashi, all of Japan

[73] Assignee: Kabushiki Kaisha Kobe Seiko Sho, Kobe, Japan

[21] Appl. No.: 448,287

[22] Filed: Dec. 11, 1989

[30] Foreign Application Priority Data

Feb. 28, 1989 [JP] Japan .................................. 1-49074
Feb. 28, 1989 [JP] Japan .................................. 1-49075
Sep. 22, 1989 [JP] Japan .................................. 1-247800

[51] Int. Cl.$^5$ .............................................. B01D 9/00
[52] U.S. Cl. ............................... 422/245; 23/295 R; 156/601; 156/623 R; 156/623 Q; 156/DIG. 93
[58] Field of Search ............... 422/245; 23/295 R; 156/601, 623 R, 623 Q, DIG. 93

[56] References Cited

U.S. PATENT DOCUMENTS

| | | | |
|---|---|---|---|
| 2,402,582 | 6/1946 | Scaff | 422/245 |
| 2,947,608 | 8/1960 | Hall | 422/245 |
| 3,206,279 | 9/1965 | Carnall | 23/295 R |
| 3,291,575 | 12/1966 | Sawyer | 156/601 |
| 3,741,656 | 6/1973 | Shapiro | 156/601 |
| 3,825,242 | 7/1974 | Menashi et al. | 422/245 |
| 4,512,846 | 4/1985 | Shlichta | 156/623 Q |

FOREIGN PATENT DOCUMENTS

| | | | |
|---|---|---|---|
| 63-182003 | 7/1988 | Japan | 23/295 R |
| 63-218105 | 9/1988 | Japan | 23/295 R |
| 63-218204 | 9/1988 | Japan | 23/295 R |

OTHER PUBLICATIONS

Pamplin, *Crystal Growth*, vol. 16, Pergamon Press, New York, 1980, pp. 359–364.

Primary Examiner—Robert Kunemund
Attorney, Agent, or Firm—Oblon, Spivak, McClelland, Maier & Neustadt

[57] ABSTRACT

A crystallographic observation apparatus for the observation of behavior of crystals under pressure and for the measurement of the crystallization pressure and pressure of fusion of substances. The apparatus comprises a pressure chamber having a cavity and provided with a transparent observation window or windows, a pressurizing device for pressurizing the cavity of the pressure vessel, and small, entirely or partly transparent, entirely or partly elastic sample containing means for containing a sample, provided within the cavity of the pressure vessel. The sample can easily be changed for another sample simply by changing the sample containing means containing the former sample for another sample containing means containing the latter sample, or the apparatus can easily be cleaned after the completion of observation of a sample for the observation of the next sample, simply by washing the sample containing means. Since the sample is contained in the small sample containing means instead of filling up the cavity of the pressure vessel and the associated piping, the apparatus requires only a small amount of sample for observation. Direct observation of the behavior of the sample under varying pressure visually, a microscope or a combination of image pickup means and display means enables the accurate measurement of the crystallization pressure and pressure of fusion of the sample.

13 Claims, 3 Drawing Sheets

OBSERVATION DIRECTION

HIGH-PRESSURE CRYSTALLOGRAPHIC OBSERVATION APPARATUS

BACKGROUND OF THE INVENTION

1. Field of the Invention

The present invention relates to a high-pressure crystallographic observation apparatus for observing the crystals of substances under a high pressure and, more specifically, to a high-pressure crystallographic observation apparatus such as for observing the forms of crystals and physical variations including processes of growth and extinction of crystals and for measuring the pressure of fusion of a solid by varying pressure at a constant temperature.

2. Description of the Related Art

Elucidation of forms of crystals and physical variations including processes of growth and extinction of crystals under pressure is very important for the manufacture or use of chemical substances under pressure.

For example, knowledge of such physical variations of crystals is an indispensable requirement of the pressure crystallization process, which has been a remarkable technique of separating a specified substance from a mixture and purifying the specified substance, because the pressure crystallization process is a separating and purifying process of producing a specified substance of high purity by separating the specified substance by crystallization from a liquid or slurry mixture by the agency of a high pressure. Accordingly, it is necessary to know in advance a pressure necessary for the separation and growth of crystals and a pressure condition for satisfactory crystallization.

Crystals are observed under pressure to obtain data representing the physical variations of the crystals under pressure.

Shown in FIG. 6 is a typical, conventional crystallographic observation apparatus for the observation of crystals under pressure. This crystallographic observation apparatus comprises a pressure vessel 130 provided with opposite, transparent observation window blocks 110 and 120 formed of a transparent material, and a pressurizing device 140 for enhancing the internal pressure of the pressure vessel 130. A pipe 150 is connected to the pressurizing device 140 to inject a sample to be observed into the pressurizing device 140. The pressurizing device 4 is connected to the pressure vessel 130 by a pressure pipe 160. The internal pressure of the pressure vessel 130 is measured by a pressure gauge 190 of an optional type connected to the pressure pipe 160.

This crystallographic observation apparatus is operated for the observation of crystals in the following manner. A sample is injected through the pipe 150 into the pressurizing device 140. The pressurizing device 140 supplies the sample through the pressure pipe 160 into the sample chamber 170 of the pressure vessel, and then the sample filled in the sample changer 170 is illuminated through the transparent observation window block 120 by a light source 180 to enable to observation of the sample with a microscope through the transparent observation window block 110.

Then, the pressurizing device 140 increases the internal pressure of the pressure vessel 130 to pressurize the sample filling the sample chamber 170. Crystallization progresses as the internal pressure is increased. The form of the crystals and the process of growth of the crystals are observed while the internal pressure of the sample chamber 170 is being increased. The process of extinction of the crystals is observed as the internal pressure of the sample chamber is decreased.

This conventional crystallographic observation apparatus, however, has the following disadvantages.

A comparatively large amount of sample is necessary to fill up the sample chamber of the pressure vessel by injecting the sample into the pressurizing device and supplying the sample through the pressure pipe to the sample chamber, because the pressurizing device and the pressure pipe must be filled up with the sample as well as the sample chamber.

In most cases, the sample for observation, as a matter of course, is a new substance, and it is difficult to prepare a large amount of such a new substance. In some cases, only a small amount of sample is available even if the sample is not a new substance. Accordingly, requiring a large amount of sample is a significant disadvantage.

A pipe having a very small inside diameter is used as the pressure pipe particularly when the crystallographic observation apparatus is used for observation under a high pressure. Therefore, a solid sample cannot be introduced in to the sample chamber. It is particularly difficult to introduce a slurry sample containing nonsoluble solid particles into the sample chamber due to high viscosity of the slurry sample.

Particularly, a liquid sample of a substance having a comparatively high melting point is liable to be caused to solidfiy within the pressure pipe even by slight decrease in temperature or by increase in pressure while the liquid sample is being injected through the pressure pipe, and often clogs the pressure pipe. Consequently, the pressurizing device is unable to increase the internal pressure of the sample chamber to a predetermined pressure. The solidification of the liquid sample may be obviated by heating the pressure pipe, which, however, may possibly entail excessive heating of the liquid sample. Accordingly, the pressure pipe must be heated for such a purpose under strict temperature control, which is very difficult. Heating the pressure pipe also heats the pressure gauge to make accurate pressure measurement impossible.

The interior of the pressurizing device, the pressure vessel and the pressure pipe must be washed perfectly after the completion of observation of a sample prior to the supply of another sample into the sample chamber of the pressure vessel, which requires much time because many parts must be washed. Washing the interior of the pressure pipe, in particular, is very difficult and requires much time because the pressure pipe has a very small inside diameter. Finish washing using the next sample requires an additional amount of sample for washing.

Furthermore, as shown in FIG. 6, the transparent observation window blocks of the conventional crystallographic observation apparatus is cylindrical and each transparent observation window block is seated on a flat seat, and hence the thickness of the transparent observation window blocks must be comparative large to secure a sufficient strength against pressure. Accordingly, the objective lens of the microscope is disposed inevitably at a comparatively long distance from the sample, so that the microscope is unable to be focused at a high magnification and hence the sample cannot sufficiently be magnified for observation.

The pressure of fusion of crystals is another very important data for the use and manufacture of a solid obtained by crystallization.

Shown in FIG. 7 is an essential portion of another conventional crystallographic observation apparatus capable of measuring the pressure of fusion. This crystallographic observation apparatus comprises, as principal components, a pressure vessel 172 having a sample chamber 182, a plunger 162 fitting the sample chamber 182, pressure measuring means, not shown, for measuring the internal pressure of the sample chamber 182, and pressing means, not shown, for pressing the plunger 162.

In measuring the pressure of fusion by the crystallographic observation apparatus, a liquid sample is poured into the sample chamber 182, the liquid sample is compressed by the plunger 162 for solidification, and then the internal pressure of the sample chamber 182 is reduced and, at the same time, the volume variation $\Delta V$ of the sample chamber 182 and the internal pressure P of the sample chamber 182 are measured to determine the relation between $\Delta V$ and P. The value of P corresponding to a point on a $\Delta V$-P curve where the volume of the sample chamber varies sharply with respect to the variation of pressure, namely, a discontinuous point on the $\Delta V$-P curve, corresponds to the pressure of fusion.

This conventional crystallographic observation apparatus, however, has the following disadvantages.

Indirectly measuring the pressure of fusion from the $\Delta V$-P relation, the crystallographic observation apparatus is unable to determine the pressure of fusion accurately, and hence this crystallographic observation apparatus has a basic problem that the accuracy of measurement is not high enough. Theoretically, a discontinuous point appears on the $\Delta V$-P curve at the pressure of fusion, howeve, practically, the gradient of the $\Delta V$-P curve in the vicinity of the pressure of fusion changes gradually instead of a sharp change and, at the worst, it occurs with some substances that the determination of the pressure of fusion is entirely impossible.

SUMMARY OF THE INVENTION

Accordingly, it is a first object of the present invention to provide a crystallographic observation apparatus requiring a small amount of sample for observation, capable of being charged with the sample comparatively easily and in a short time, capable of constantly regulating the pressure of the sample at a set value, eliminating the need of heating of the pressure pipe, capable of keeping the sample at a set temperature, and capable of comparatively easily being washed perfectly.

It is a second object of the present invention to provide a crystallographic observation apparatus capable of accurately measuring the pressure of fusion of a substance using a compartively small amount of sample even if the substance does not have a distinct point of discontinuity on the $\Delta V$-P curve In a first aspect of the present invention, a crystallographic observation apparatus comprises a pressure vessel having a cavity and provided with transparent observation window blocks repsectively in the opposite walls thereof, a small elastic vessel defining a sample chamber in the cavity together with one of the transparent observation window blocks to seal a sample in a pressure-tight fashion, and pressurizing device means for enhancing the internal pressure of the cavity of the pressure vessel.

The pressure increasing means supplies a pressure medium through a pressure pipe to the cavity of the pressure vessel and pressurizes the pressure medium to a set pressure to pressurize the small elastic vessel, so that internal pressure of the sample chamber is increased to apply the set pressure to the sample contained in the sample chamber. Similarly, a set pressure can be applied to the sample by decreasing the internal pressure of the cavity to the set pressure after increasing the internal pressure to a higher set pressure.

The sample is illuminated from outside the sample chamber through the transparent observation window block defining the sample chamber. When the elastic vessel is formed of a transparent material or is provided with a transparent window, the sample can be illuminated through one of the transparent observation window blocks and can be observed through the other transparent observation window block.

Since the sample is sealed in a pressure-tight fashion in the sample chamber, the sample is never contaminated by the pressure medium and the purity of the sample can be kept at the initial purity.

Since the volume of the sample chamber is far smaller than that of the cavity of the pressure vessel corresponding to the sample chamber of the pressure vessel of the conventional crystallographic observation apparatus, the crystallographic observation apparatus of the present invention needs only a very small amount of sample for observation.

The small elastic vessel containing the sample is placed in the cavity of the pressure vessel in charging the pressure vessel with the sample. According, even solid samples and slurry samples, which are difficult to put in the sample chamber in a short time similarly to liquid samples. This manner of placing a sample in the sample chamber solves the problem that a sample having a high melting point is solidified in the pressure pipe and clogs the pressure pipe to make the application of a test pressure to the sample impossible, because the sample is contained beforehand in the sample chamber and a pressure medium hard to solidify can be used. Accordingly, the pressure pipe need not be heated, there is little apprehension of the physical properties of the sample being changed by heat and deterioration of the accuracy of the pressure gauge by heat, so that pressure acting on the sample can accurately be measured.

Since the sample is sealed in the sample chamber defined by the transparent observation window block and the small elastic vessel, only the transparent observation window block and the small elastic vessel need to be washed, or another small elastic vessel is used and only the transparent observation window block is washed for the observation of another sample.

In a second aspect of the present invention, a crystallographic observation apparatus comprises a pressure vessel having a cavity and provided with a transparent observation window block in one side wall thereof, a small, sealed elastic capsule for containing a sample, provided with a transparent window at least in its side wall facing the transparent observation window block and to be placed in the cavity of the pressure vessel, and pressurizing means for pressurizing the cavity of the pressure vessel. Accordingly, only the small, sealed elastic capsule must be washed or another small, sealed elastic capsule is used for the observation of another sample. The sample is illuminated through the transparent observation window block and the transparent wall of the small, sealed elastic capsule for observation. The pressure vessel may be provided with another transparent observation window block in a wall opposite the wall in which the former transparent observation window block is provided. In such a case, the small, sealed elastic capsule is formed of a transparent material or both the side walls respectively facing the transparent observation window blocks are formed of a transparent material. Such a small, sealed elastic capsule enables the illumination of the sample through one of the transparent observation window blocks and the observation of the sample through the other transparent observation window block.

The transparent observation window blocks may be formed of any material in any shape provided that a sufficiently high transmissivity and a sufficient strength are secured. The transparent observation window blocks, for example, are semispherical or cylindrical blocks of sapphire, a hard optical glass or a hard optical plastic. Preferably, the transparent observation window blocks are semispherical blocks placed in the pressure vessel with their circular flat surfaces on the inner side of the pressure vessel. The thickness of such a semispherical transparent observation window block sufficient to ensure the strength of the transparent observation window block to withstand an operating pressure is comparatively small, so that the microscope can be disposed with its objective lens at a comparatively short distance from the sample, and hence the microscope can be focused at a high magnification to observe the sample at a sufficiently high magnification.

The small elastic capsule need not entirely be formed of an elastic material, but may have an elastic portion which extends or contracts elastically to vary the volume of the small elastic capsule. Shown in FIG. 2 is a sample chamber defined by a cylindrical transparent window block 164 and a small, bottomed cylindrical container formed by connecting a transparent bottom member 184 to an elastic cylindrical member 174. The elastic cylindrical member 17 expands or contracts according to pressure that acts thereon. The bottom member 184 need not necessarily be formed of a transparent material. The small elastic capsule must be elastic and transparent. However, the small elastic capsule need not entirely be formed of a transparent material. For example, a small capsule as shown in FIG. 4 may be employed. This small capsule comprises a cylindrical elastic member 176, a bottom member 186 joined to the lower end of the cylindrical elastic member 176, and a transparent disk 206 joined to the upper end of the cylindrical elastic member 176. The cylindrical elastic member 176 and the bottom member 186 may be either transparent or opaque.

The elastic portion of the small, elastic capsule may be formed, for example, of silicon rubber or a polyethylene resin. There is no particular restriction on the material of the elastic portion provided that the mateiral is elastic. The shape of the elastic vessel may be a flanged rectangular parallelpiped or a flanged semisphere. The elastic vessel may be provided partially with a bellows. The shape of the elastic capsule may be a rectangular parallelepiped or a sphere. However, there is no particular restriction on the shapes of the elastic vessel and the elastic capsule.

In measuring the pressure of fusion of the sample, the internal pressure of the pressure vessel is increased to solidify the sample, and the sample is observed as the internal pressure of the pressure vessel is decreased gradually. Thus, a pressure at the completion of fusion of the solidified sample, i.e., the pressure of fusion, can surely be measured at a high accuracy even if the ΔV-P curve of the sample does not have a sharp point of discontinuity.

Although the sample may be observed with the eye, desirably, the crystallographic observation apparatus is provided with photographing means, such as a TV camera, and display means, such as a TV monitor, capable of displaying the image of the sample and numerical data indicating the temperature and the pressure within the pressure vessel to facilitate the observation of the sample and to achieve the observation of the sample at a satisfactory accuracy. Such means magnifies the sample and enables the observation in an easy position.

Desirably, the crystallographic observation apparatus is provided with recording means, such as a video tape recorder, for recording the image of the sample. The record enables the review of the results of observation and the automatic measurement of the pressure of fusion.

Since the transmissivity of the sample changes sharply when the sample changes from a solid phase to a liquid phase, the pressure of fusion can be determined from the measurement of the internal pressure at which the transmissivity of the sample changes sharply. Therefore, the crystallographic observation apparatus may be provided with transmissivity measuring means near one of the transparent observation window blocks.

BRIEF DESCRIPTION OF THE DRAWINGS

The above and other objects, features and advantages of the present invention will become more apparent from the following description taken in conjunction with the accompanying drawings, in which.

DETAILED DESCRIPTION OF THE PREFERRED EMBODIMENTS

Figure 1:
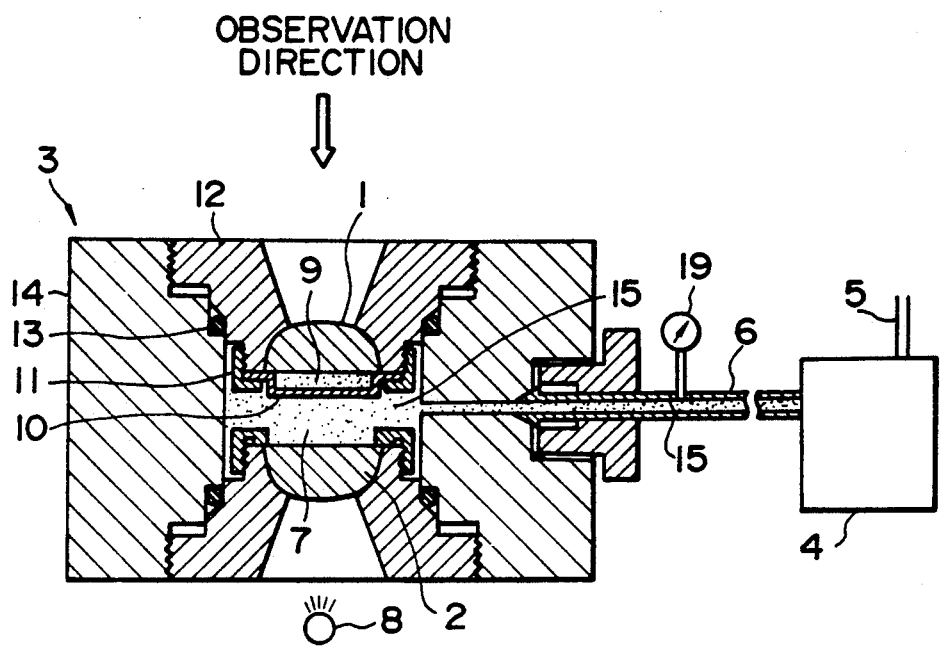
FIG. 1 is a sectional view of a crystallographic observation apparatus in a first embodiment according to the present invention.
Figure 2:
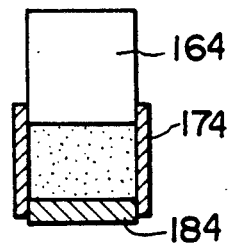
FIG. 2 is a sectional view of an elastic vessel which may be employed in the crystallographic observation apparatus of FIG. 1.
Figure 4:
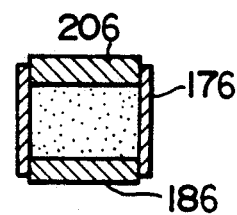
FIG. 4 is a sectional view of a small elastic capsule which may be employed in the crystallographic observation apparatus of FIG. 3.

First Embodiment (FIGS. 1, 2)

Referring to FIG. 1, a crystallographic observation apparatus comprises a pressure vessel 3 having a cavity 7, a pressurizing device 4 for pressurizing the pressure vessel 3, and a pressure pipe 6 connecting the pressurizing device 4 to the pressure vessel 3. A pipe 5 is connected to the pressurizing device 4 to supply a pressure medium 15 to the pressurizing device 4.

The pressure vessel 3 is provided with a first semispherical observation window block 1 and a second semispherical observation window block 2 respectively in the upper and lower side walls thereof. The first and second observation window blocks 1 and 2 are formed of sapphire and are held in place by observation window block holding members 12 with their flat circular surfaces facing the cavity 7 of the pressure vessel 3. The observation window block holding members 12 are screwed in the pressure vessel 3. O rings 13 are provided to seal the interfaces between the observation window block holding members 12 and the body 14 of the pressure vessel 3. The central portions of the spherical surfaces of the first and second observation window blocks 1 and 2 are flattened to enable the exact observation of a sample.

A small, transparent elastic vessel 10 is formed entirely of silicon rubber. The flange of the elastic vessel 10 is pressed firmly against the periphery of the flat circular surface of the first observation window block 1 and the lower end of the observation window block holding member 12 by a fastening ring 11 screwed on the lower portion of the observation window block holding member 12 to form a pressure-tight sample chamber 9 defined by the first observation window block 1 and the elastic vessel 10. The sample is sealed in the sample chamber. The pressurizing device 4 is connected by a pressure pipe 6 to the pressure vessel 3, and a strain gauge pressure sensor 19 is provided on the pressure pipe 6.

The process of crystallization of a liquid sample was observed by the crystallographic observation apparatus. In observing the process of crystallization of the liquid sample, the pressure medium 15 was supplied by the pressurizing device 4 to the pressure vessel 3 to fill up the cavity 7. The liquid sample was illuminated through the second observation window block 2 by a light source 8 for observation by an optical microscope, not shown, disposed outside the pressure vessel 3 near the first observation window block 1. Then, the cavity 7 was pressurized by increasing the pressure of the pressure medium 15 filled in the cavity 7 by the pressurizing device 4 to apply increasing pressure to the liquid sample. As the internal pressure of the cavity 7 increased, the elastic vessel 10 was caused to contract gradually and crystals began to form in the liquid sample when the internal pressure of the cavity 7 reached the crystallization pressure. The crystallization pressure measured by the crystallographic observation apparatus was equal to that measured by the conventional crystallographic observation apparatus.

A sample having a pressure of fusion, the accurate value of which (hereinafter referred to as "reference value") is known, was subjected to the measurement of the pressure of fusion by the crystallographic observation apparatus. The pressure medium 15 was supplied through the pressure pipe 6 to the pressure vessel 3 by the pressurizing device 4 to fill up the cavity 7 of the pressure vessel 3 with the pressure medium 15 and the sample was illuminated through the second observation window block 2 by the light source 8. The condition of the sample was observed through the first observation window block 1.

Then, the pressure of the pressure medium 15 filled in the cavity 7 was increased gradually by the pressurizing device 4 to apply pressure to the sample. The elastic vessel 10 contracted gradually as the pressure of the pressure medium 15 was increased. The internal pressure of the sample chamber 9 was measured by the strain gauge pressure sensor 19 provided on the pressure pipe 6. The internal pressure of the sample chamber 9 was increased to a level where the sample was solidified, and then the internal pressure of the sample chamber 9 was decreased gradually. While the internal pressure of the sample chamber 9 was being decreased, the internal pressure of the sample chamber was measured continuously by the strain gauge pressure sensor 19 and the condition of the sample was observed. The measured pressure of fusion thus determined was higher than the reference value only by 0.2% of the reference value. This measured pressure of fusion is very accurate as compared with that measured by the conventional crystallographic observation apparatus, which is higher than the reference value by 2.5% of the reference value.

Figure 3:
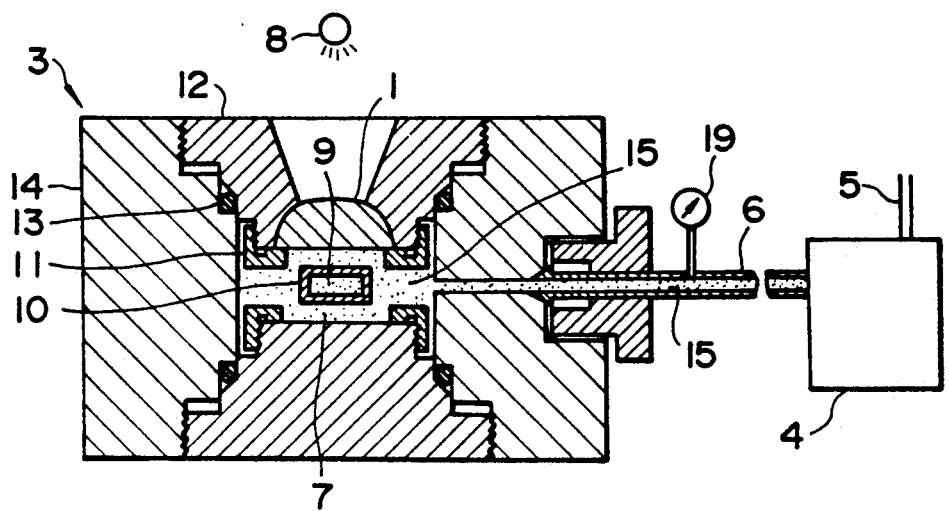
FIG. 3 is a sectional view of a crystallographic observation apparatus in a third embodiment according to the present invention.

Second Embodiment (FIG. 3)

A crystallographic observation apparatus in a second embodiment according to the present invention is substantially the same in construction and function as the crystallographic observation apparatus in the first embodiment, except that a pressure vessel employed in the second embodiment is provided with only one observation window block 1, and an opaque elastic vessel 10 having a transparent window is employed. The crystallographic observation apparatus in the second embodiment employs a reflection optical microscope instead of a transmission optical microscope for the observation of the sample. The performance of this crystallographic observation apparatus was the same as that of the foregoing crystallographic observation apparatus in the first embodiment.

Third Embodiment (FIG. 3)

A crystallographic observation apparatus in a third embodiment according to the present invention is substantially the same in construction and function as the crystallographic observation apparatus in the first embodiment, except that a pressure vessel 3 employed in the third embodiment is provided with only one observation window block 1, and a small, transparent elastic capsule 10 is employed for containing a sample. The crystallographic observation apparatus in the third embodiment employs a reflection optical microscope instead of a transmission optical microscope for the observation of the sample. The upper wall of the elastic capsule 10 facing the observation window block 1 is formed of a transparent material and the rest of the walls are formed of an opaque elastic material.

The satisfactory performance of the crystallographic observation apparatus in the observation of the sample and in the measurement of the pressure of fusion of the sample was the same as that of the crystallographic apparatus in the first embodiment.

Figure 5:
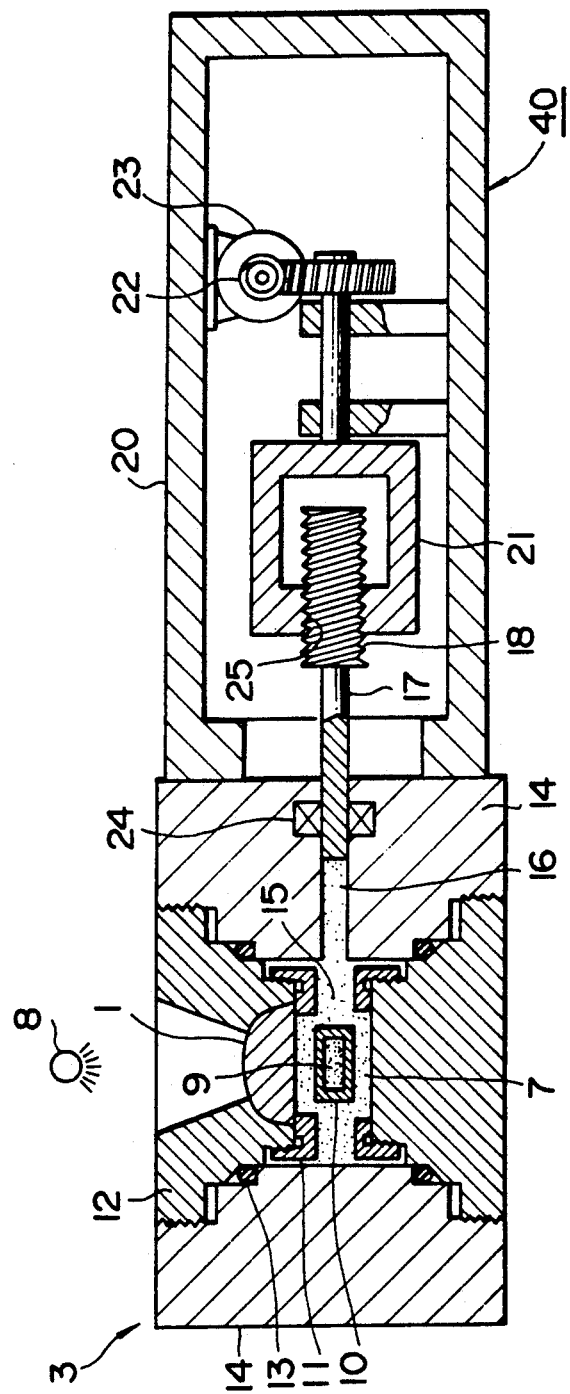
FIG. 5 is a sectional view of a crystallographic observation apparatus in a in a fourth embodiment according to the present invention.
Figure 6:
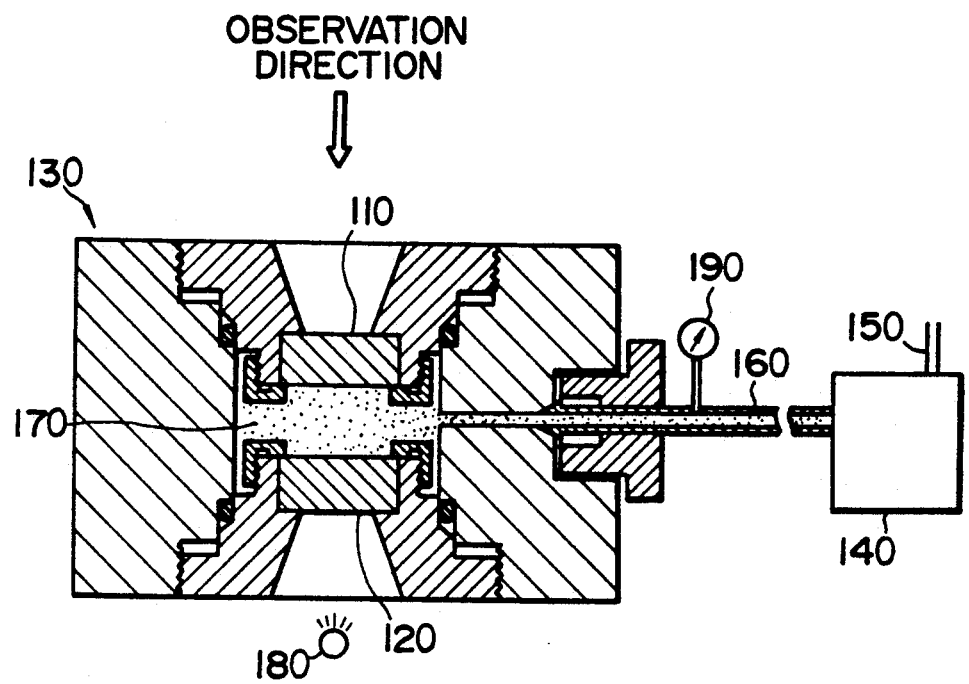
FIG. 6 is a sectional view of a conventional crystallographic observation apparatus.
Figure 7:
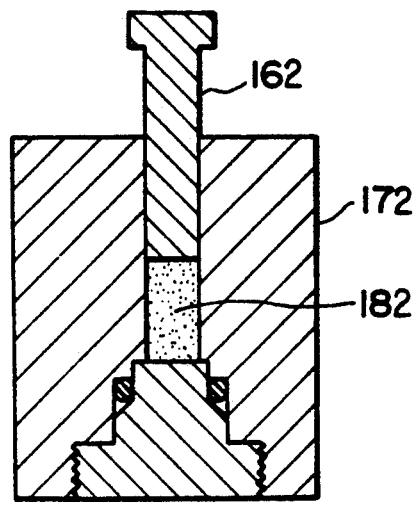
FIG. 7 is a sectional view of an essential portion of another conventional crystallographic observation apparatus.

Fourth Embodiment (FIG. 5)

Referring to FIG. 5, a crystallographic observation apparatus in a fourth embodiment according to the present invention comprises a pressure vessel 3 having a cavity 7, and a pressurizing device 40 directly connected to the pressure vessel 3. The pressure vessel 3 is substantially the same in construction and configuration as that of the crystallographic observation apparatus in the third embodiment, and hence the description thereof will be omitted to avoid duplication.

The pressurizing device 40 comprises a plunger 17 fitted in a through hole 16 formed in one side wall 14 of the pressure vessel 3 so as to communicate with the cavity 7 of the pressure vessel 3, and a driving mechanism 20 for driving the plunger 17. Indicated at 24 is a pressure-tight sealing member.

The driving mechanism 20 comprises an electric motor 23, a worm reduction gear 22 having a worm fixedly mounted on the output shaft of the electric motor 23 and a worm wheel engaging the worm and fixedly mounted on one end of a driving shaft, and a screw-nut pressing mechanism comprising an internally threaded rotary member 21 attached to the other end of the driving shaft, and a screw rod 18 engaging the internal thread 25 of the rotary member 21 and joined to the plunger 17. The plunger 17 is driven for movement toward or away from the cavity 7 through the worm reduction gear 22 and the screw-nut pressing mechanism by the electric motor 23 to apply pressure to or to relieve pressure from a pressure medium 15 filling up the cavity 7 and the through hole 16.

A small, elastic capsule 10 for containing a sample is formed entirely of transparent silicon rubber. A sample is contained in the sample chamber 9 of the elastic capsule 10.

In observing the condition of the sample contained in the elastic capsule 10 placed in the cavity 7 of the pressure vessel 3, the sample is illuminated through the observation window block 1 by a light source 8, the pressure medium 15 is filled in the cavity 7 and the through hole 16, and then the plunger 17 is advanced by the electric motor 23 to apply pressure to the sample contained in the sample chamber 9 of the elastic capsule 10 by pressurizing the pressure medium 15 filled in the cavity 7 and the through hole 16. The condition of the sample under pressure is observed with an optical microscope, not shown, through the observation window block 1.

In determining the crystallization pressure and pressure of fusion of the sample, a pressure at which crystallization occurs is determined while the pressure in the cavity 7 is increased to a high pressure level where the sample is solidified, and the pressure of fusion is determined while the pressure is decreased gradually from the high pressure level.

The practical operation of the crystallographic observation apparatus showed that the performance of the crystallographic observation apparatus in the fourth embodiment in determining the crystallization pressure and the pressure of fusion is the same as those of the foregoing embodiments.

The worm reduction gear 22 may be driven by a manual driving mechanism instead of the electric motor 23. However, the use of the electric motor 23 for driving the worm reduction gear 22 makes possible discretionary pressure control, pressurization at a constant rate and employment of a computer for complicated pressure regulation.

This crystallographic observation apparatus needs a comparatively small amount of pressure medium necessary for filling up only the cavity 7 and the through hole 16, so that the pressurizing device 40 may be of a comparatively small capacity or the pressure medium can be pressurized or the pressure applied to the pressure medium can be decreased in a comparatively short time.

Since the pressurizing device 40 is connected directly to the pressure vessel 3 omitting a pressure pipe and the pressurizing system employing the plunger 17 is inherently resistant to the leakage of the pressure medium, there is the least possibility of the leakage of the pressure medium.

Since the pressurizing device 40 is connected directly to the pressure vessel 3 without using any pipe, the plunger 17 is fitted in the through hole 16 formed in the side wall 14 of the pressure vessel 3, and only the driving mechanism is disposed outside the pressure vessel 3, the crystallographic observation apparatus including the pressuring device can be formed in a compact construction.

As is apparent from the foregoing description, the crystallographic observation apparatus in accordance with the present invention requires a comparatively small amount of sample, facilitates the placement of the sample in the cavity of the pressure vessel, enables the placement of the sample in the cavity of the pressure vessel in a comparatively short time, is capable of accurately regulating the pressure applied to the sample, eliminates heating the sample in introducing the sample in the cavity of the pressure vessel, is capable of being washed comparatively easily for the subsequent observation of the next sample, and enables the microscope to be disposed with the objective lens thereof at a comparatively short distance from the sample for the observation of the sample at a high magnification.

Although the invention has been described in its preferred forms with a certain degree of particularity, obviously many changes and variations are possible therein. It is therefore to be understood that the present invention may be practiced otherwise than as specifically described herein without departing from the scope and spirit thereof.

What is claimed is:

1. A high-pressure crystallographic observation apparatus comprising:
   a pressure vessel having a cavity and provided with transparent observation window blocks respectively in the opposite walls thereof;
   pressurizing means for pressurizing the cavity of the pressure vessel; and
   small elastic sample containing means for containing a sample, provided within the cavity of the pressure vessel.

2. A high-pressure crystallographic observation apparatus according to claim 1, including photometric means is provided near one of the transparent observation window blocks to measure the intensity of light transmitted through the sample.

3. A high-pressure crystallographic observation apparatus according to claim 1, wherein said sample containing means comprises a small elastic vessel defining a sample chamber in the cavity of the pressure vessel together with one of the transparent observation window blocks.

4. A high-pressure crystallographic observation apparatus comprising:
   a pressure vessel having a cavity and provided with a transparent observation window block in one of the walls thereof;
   pressurizing means for pressurizing the cavity of the pressure vessel; and
   small elastic sample containing means for containing a sample, provided within the cavity of the pressure vessel.

5. A high-pressure crystallographic observation apparatus according to claim 4, wherein said small elastic sample containing means comprises a small elastic vessel defining a sample chamber in the cavity of the pressure vessel together with the transparent observation window block.

6. A high-pressure crystallographic observation apparatus according to claim 4, wherein said small elastic sample containing means is a small elastic capsule provided with a transparent window in the wall thereof facing the transparent observation window block of said pressure vessel.

7. A high-pressure crystallographic observation apparatus according to claim 1 or 4, further comprising pressure measuring means for measuring the pressure acting on the sample contained in the small elastic sample containing means.

8. A high-pressure crystallographic observation apparatus according to claim 1 or 4, wherein each transparent observation window block has a semispherical shape and is disposed with the flat circular surface thereof facing the cavity of the pressure vessel.

9. A high-pressure crystallographic observation apparatus according to claim 1 or 4, wherein said pressurizing means comprises a plunger fitted in a through hole formed in the side wall of said pressure vessel so as to communicate with the cavity, and driving means for driving the plunger for axial movement toward or away from the cavity.

10. A high-pressure crystallographic observation apparatus according to any one of claim 1 or 4, further comprising image pickup means disposed near the transparent observation window block, display means for displaying the image of the sample taken by the image pickup means, and indicating means for indicating numerical data representing the pressure acting on the sample and the temperature of the sample on the display means.

11. A high-pressure crystallographic observation apparatus according to claim 10, further comprising recording means for recording the image of the sample taken by said image pickup means.

12. A high pressure crystallographic observation apparatus according to claim 1, wherein the sample containing means is formed of silicon rubber.

13. A high pressure crystallographic observation apparatus according to claim 4, wherein the sample containing means is formed of silicon rubber.

* * * * *